United States Patent
Paciello et al.

(10) Patent No.: US 6,255,532 B1
(45) Date of Patent: Jul. 3, 2001

(54) METHOD FOR PRODUCING PHOSPHABENZENE COMPOUNDS

(75) Inventors: Rocco Paciello, Bad Dürkheim; Edgar Zeller, Mannheim; Bernhard Breit, Marburg; Michael Röper, Wachenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/509,672
(22) PCT Filed: Sep. 30, 1998
(86) PCT No.: PCT/EP98/06216
  § 371 Date: Mar. 30, 2000
  § 102(e) Date: Mar. 30, 2000
(87) PCT Pub. No.: WO99/16774
  PCT Pub. Date: Apr. 8, 1999

(30) Foreign Application Priority Data

Sep. 30, 1997 (DE) ............................... 197 43 197

(51) Int. Cl.$^7$ .................................... C07F 9/50
(52) U.S. Cl. ................ 568/12; 562/30; 564/16; 560/8
(58) Field of Search ............... 568/12; 560/8; 562/30, 35; 564/16

(56) References Cited

FOREIGN PATENT DOCUMENTS

| | | |
|---|---|---|
| 16 18 668 | 2/1971 | (DE) . |
| 16 68 413 | 8/1971 | (DE) . |
| 196 21 967 | 12/1997 | (DE) . |
| 197 43 197 | 4/1999 | (DE) . |

OTHER PUBLICATIONS

Angewandte Chemie "Derivate des Phrosphorins aus Pyryliumsalzen und Phosphorwasserstoff" by Markl et la vol. 79, No. 21, pp. 947–948, 1967.*
CA:67:32737 abs of Angew Chem Int. Ed. Engl. by Maerkl 6(5) pp 458–9, 1967.*
CA:66:38010 abs of Angew Chem by Maerkl et al 78(18–19) pp 907–8, 1966.*
CA:123:144038 abs of Tetrahedron Lett by Maerkl et al 36(22) pp 3839–42, 1995.*
CA:72:100819 abs of Tetrahedron Lett by Maerkl et al (9) pp 645–8, 1970.*
CA:84:17503 abs of Chem Ber by Schaffer 108(10) pp 3271–80, 1975.*
CA:80:146241 abs of Angew Chem by Kieselack 86(3) pp 129–120, 1974.*
F. Lieb,, "Synthesne und Reaktionen von Phosphirinen, Untersuchungen zur Drstellung on Systemen mit Arsen-–Kohlenstoff–Doppelbindungen", Inaugural Thesis, Wurzburg, 1969, pp. 106–107.

* cited by examiner

Primary Examiner—Jean F. Vollano
(74) Attorney, Agent, or Firm—Keil & Weinkauf

(57) ABSTRACT

A process for the preparation of phosphabenzene compounds of the formulae I and II

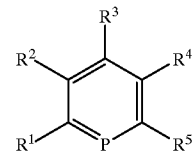

(I)

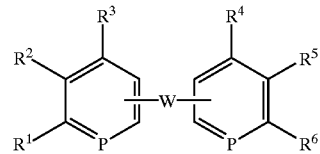

(II)

where $R^1$ to $R^6$, independently of one another, are hydrogen, COOM $SO_3M$, $NR_3X$, $NR_2$, OR, COOR or SR, where M is hydrogen, $NH_4$ or an alkali metal, X is an anion, R is hydrogen, $C_{1-6}$-alkyl, or $C_{1-12}$-alkyl, $C_{6-12}$-aryl, $C_{7-12}$-aralkyl or $C_{3-6}$-heterocycloalkyl having 1 to 3 heteroatoms which may be substituted by the above radicals or linked to form fused rings, and —W— is a bridge comprising a covalent bond, an oxo group, a sulfur group, an amino group, a di-$C_{1-6}$-alkylsilicon group or a $C_{1-16}$-radial, which may be part of one or more linked cyclic or aromatic rings and may be interrupted by 1 to 3 heteroatoms, where the phosphabenzene ring o- or m-position not bonded to the bridge may carry one of the radicals $R^1$ to $R^6$, with the exception of bis-3,3'-(2,4,6-triphenyl-3-phosphabenzene)-1,1-biphenyl, by reacting corresponding pyrilium salts with $PH_3$ in the presence of a catalytic amount of acid and in the presence or absence of a solvent or diluent, where the pyrilium salts are mixed with $PH_3$ at above 0° C. and reacted at from 0° C. to 200° C. and at a pressure greater than 1 bar.

8 Claims, No Drawings

METHOD FOR PRODUCING PHOSPHABENZENE COMPOUNDS

This is the national phase of PCT/EP 98/06216, filed Sep. 30, 1998, now WO 99/16774.

Phosphabenzene compounds can be used as ligands in transition-metal complexes used in the hydroformylation of olefins. In DE-A 196 21 967, having the title "Hydroformylation process, and catalysts containing phosphorus compounds as ligands which are suitable therefor", which has an earlier priority date, but was not published before the priority date of the present application, corresponding complexes and processes for their preparation are described. According to one process variant, bis-3,3'-(2,4,6-triphenyl-3-phosphabenzene)-1,1'-biphenyl can be prepared by reacting the corresponding pyrilium salt with phosphine.

DE-A 1 618 668 describes a process for the preparation of substituted phosphabenzenes in which pyrilium salts are reacted with trishydroxymethylphosphine, trishydroxymethylphosphine chloride or tetrahydroxymethylphosphine hydroxide. The phosphine compounds are difficult to prepare, and the process is uneconomical.

F. Lieb, "Synthesen und Reaktionen von Phosphorinen, Untersuchungen zur Darstellung von Systemen mit Arsen-Kohlenstoff-Doppelbindungen" [Syntheses and Reactions of Phosphorins, Studies on the Preparation of Systems Containing Arsenic-Carbon Double Bonds], inaugural dissertation, Wiirzburg, 1969, pages 106 and 107, describes a process for the preparation of 2,4,6-triphenylphosphorin (2,4,6-triphenylphosphabenzene), in which 2,4,6-triphenylpyrilium tetrailoroborate in n-butanol is reacted at −78° C. with $PH_3$, which dissolves in the diluent. After the reaction vessel has been sealed, the reaction proceeds for 41 hours at 110° C. under autogenous pressure.

Carrying out the reaction under autogenous pressure has the disadvantage that the concentration of the reactants changes constantly and long reaction times are necessary. The introduction of $PH_3$ at −78° C. requires the use of corresponding cooling equipment. The process in a sealed reaction vessel is difficult or impossible to control.

It is an object of the present invention to provide a process for the preparation of phosphabenzene compounds which is economical and avoids the disadvantages of the known processes.

We have found that this object is achieved by a process for the preparation of phosphabenzene compounds of the formulae I and II

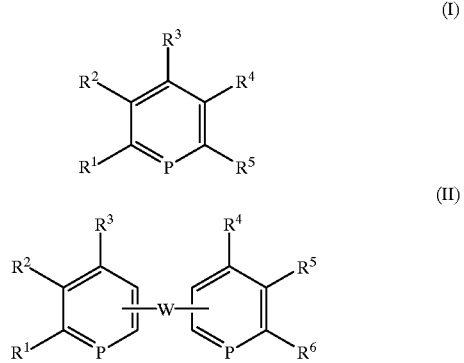

where $R^1$ to $R^6$, independently of one another, are hydrogen, COOM, $SO_3M$, $NR_3X$, $NR_2$, OR, COOR or SR, $C_1$-$C_{12}$-alkyl, $C_6$-$C_{12}$-aryl, $C_7$-$C_{12}$-aralkyl, or $C_{3-6}$-heterocycloalkyl having 1 to 3 heteroatoms, and wherein $C_1$-$C_{12}$-alkyl, $C_6$-$C_{12}$-aryl, $C_7$-$C_{12}$-aralkyl, or $C_{3-6}$-heterocycloalkyl are optionally substituted by COOM, S03M, $NR_3X$, $NR_2$, OR, COOR or SR where M is hydrogen, $NH_4$ or an alkali metal, X is an anion, R is hydrogen, $C_{1-6}$-alkyl, or $C_{1-12}$-alkyl, $C_{6-12}$-aryl, $C_{7-12}$-aralkyl or $C_{3-6}$-heterocycloalkyl having 1 to 3 heteroatoms which may be substituted by the above radicals or linked to form fused rings, and W is a bridge comprising a covalent bond, an oxo group, a sulfur group, an amino group, a di-$C_{1-6}$-alkylsilicon group or a $C_{1-16}$-radical, which may be part of one or more linked cyclic or aromatic rings and may be interrupted by 1 to 3 heteroatoms, where the phosphabenzene ring o- or m-position not bonded to the bridge may carry one of the radicals $R^1$ to $R^6$, with the exception of bis-3,3'-(2,4,6-triphenyl-3-phosphaphenyl)-1,1'-biphenyl, by reacting corresponding pyrilium salts with $PH_3$ in the presence of a catalytic amount of acid and in the presence or absence of a solvent or diluent. In the novel process, pyriliwn salts are mixed with PH3 at above 0° C. and reacted at from 0° C. to 200° C. and at a pressure greater than 1 bar.

It has been found in accordance with the invention that phosphabenzene compounds of the above formulae are obtainable by reacting the corresponding pyrilium salts, i.e. compounds in which phosphorus in the formulae I and II has been replaced by $O^+$ with a corresponding counterion, with $PH_3$ if certain process conditions are observed. The pyrilium salts are commercially available or can easily be prepared. $PH_3$ is commercially available.

The reaction is preferably carried out at a $PH_3$ partial pressure in the range from 0.1 to 100 bar, particularly preferably in the range from 5 to 35 bar, in particular in the range from 20 to 30 bar. The overall pressure in the system depends on the particular solvent. The overall pressure can be increased by injecting $PH_3$ or an inert gas.

In a preferred procedure, $PH_3$ is passed into the reaction mixture during the reaction in order to keep the $PH_3$ partial pressure essentially constant. This procedure allows a particularly economical and fast reaction to give the desired phosphabenzene compounds. High product purities and conversions are achieved. The novel process can be employed reliably for a multiplicity of products. It can be carried out continuously or batchwise, preferably batchwise.

In a particularly advantageous process variant, the pyrilium salts are mixed with $PH_3$ at ambient temperature, and the resultant mixture is heated to a temperature in the range from 110 to 130° C. for the reaction.

The temperature during the reaction is particularly preferably from 115 to 125° C. The reaction is preferably carried out in an autoclave. Besides $PH_3$, it is also possible tadditionally to use an inert gas to set the desired overall pressure. However, it is preferred to use $PH_3$ alone.

The reaction can be carried out in the presence or absence of a solvent or diluent. It is preferably carried out in the presence of a solvent or diluent Suitable solvents or diluents are, for example, lower aliphatic alcohols, such as methanol, ethanol, n-propanol, i-propanol, n-butanol, i-butanol, tert-butanol or pentanol isomers, preferably ethanol, propanol or butanols, in particular n-butanol.

The reaction is preferably carried out in the presence of an acidic catalyst. Suitable acidic catalysts are mineral acids, such as HI, HCl or HBr. In particular, hydrogen bromide in acetic acid or acetic anhydride is used as the acidic catalyst.

After the reaction, the reaction mixture is preferably decompressed and, if desired, flushed with an inert gas. In order to remove unreacted $PH_3$ in liquid form, the gases leaving the reaction mixture are cooled and passed through a separator, and the $PH_3$ removed is fed back into the reaction.

A particularly economical and ecologically acceptable process is therefore one in which $PH_3$ is passed into a reactor, the reaction is carried out, and the gas stream is passed, via a further line, through a condenser of any desired design, in which the $PH_3$ is condensed out. In a downstream separator of any desired design, the $PH_3$ is then separated off and fed back into the reaction, for example with the aid of a pump. In order to obtain an offgas which is particularly low in $PH_3$, it is advantageous to use a second downstream condenser and separator. In order completely to free the reactor gas space and the apparatuses employed from $PH_3$, which is advantageous owing to the toxicity of $PH_3$, a flushing line for flushing with an inert gas, such as nitrogen, should be provided. The flushing gas should be passed through the combination of condenser and separator.

The time needed for the reaction depends on the nature of the pyrilium salt. Depending on the pyrilium salt, the reaction is preferably carried out for a period of from 1 to 4 hours. The proportion of solvent, based on the pyrilium salts employed, is preferably from 5 to 50% by weight, particularly preferably from 15 to 35% by weight. The amount of acidic catalyst employed is, based on the pyrilium salts, preferably from 0.01 to 1%, particularly preferably from 0.03 to 0.1%. In the case of reaction using a solvent, the concentration of $PH_3$ in the solvent depends on the $PH_3$ partial pressure and the nature of the solvent; in particular in the case of a continuous reaction procedure, a high concentration of $PH_3$ in the solvent should be maintained.

In order to achieve high conversions in a short reaction time, it is preferred to use high $PH_3$ pressures and to continuously re-inject $PH_3$.

The novel process can be carried out using a multiplicity of different pyrilium salts. The process is in general not restricted to certain classes of compound. For example, the pyrilium salts can be ferrates, zincates, chlorides, borates, if desired containing a $C_{1-6}$-alkyl radical, triflates, trifluoroacetates or preferably tetrafluoroborates, perchlorates, hydrogensulfates, bromides, iodides, or mixtures thereof. Tetrafluoroborates are preferred. The organic radical in the pyrilium salts employed in accordance with the invention is described in greater detail below with reference to the phosphabenzene compounds prepared therefrom.

In the above compounds of the formula I, the radicals $R^1$ to $R^5$, independently of one another, are hydrogen, COOM, $SO_3M$, $NR_3X$, $NR_2$, OR, COOR or SR, where M is hydrogen, $NH_4$ or an alkali metal, X is an anion, R is hydrogen or $C_{1-6}$-alkyl, or $C_{1-12}$-alkyl, $C_{6-12}$-aryl, $C_{7-12}$-aralkyl or $C_{3-6}$-heterocycloalkyl having 1 to 3 heteroatoms, where the alkyl, aryl and aralryl radicals may be substituted by the abovementioned radicals or linked to form fused rings. The radicals $R^1$ to $R^5$ may be identical or different. $R^1$ to $R^5$ are preferably alkyl, aryl or aralkyl radicals, which may be substituted.

If two or more of the radicals are linked to form fused rings, the compounds can be phosphanaphthalene or higher aromatic compounds. The radicals are preferably $C_{6-12}$-aryl radicals, particularly preferably phenyl radicals, or, $C_{7-12}$-aralkyl radicals, particularly preferably benzyl radicals.

Particular preference is given to compounds of the formula I which are substituted in the ortho-positions and/or para-positions by substituted or unsubstituted phenyl radicals. In particular, all the ortho- and para-positions are substituted by phenyl radicals. These radicals preferably have no further substituents or one fiurther substituent. These substituents are preferably an acid or amino radical, if desired in salt form, which is in particular in the para-position. In addition, one or both meta-positions can be substituted by a benzyl radical.

In the compounds of the formula II, $R^1$ to $R^6$ are as defined above. —W— denotes a bridge comprising a covalent bond, an oxo group, a sulfur group, an amino group, a di-$C_{1-6}$-alkylsilicon group or a $C_{1-6}$-radial, preferably $C_{1-6}$-radical, which may be part of one or more linked, cyclic or aromatic rings and may be interrupted by 1 to 3 heteroatoms, where each phosphabenzene ring o- or m-position which is not bonded to the bridge can carry one of the radicals $R^1$ to $R^6$.

The bridge W can be, for example, a substituted or unsubstituted methylene group of the formula $CR^7R^8$, where $R^7$ and $R^8$ may be identical or different and can be hydrogen or alkyl radicals having a total of 1 to 15 carbon atoms or phenyl radicals, or alternatively alkaryl or aralkyl radicals so long as the radical does not have more than 16 carbon atoms.

In addition, —W— can be an oxa group (—O—), sulfuir group (—S—), di-$C_{1-6}$-alkylsilicon group (—Si(alkyl)$_2$—) or an amino group —$NR^9$—, where $R^9$ is $C_{1-6}$-alkyl, $C_{6-12}$-aryl or $C_{7-15}$-aralkyl, in particular benzyl.

—W— can contain one or more linked cyclic or aromatic rings, particularly preferably one or two cyclic or aromatic rings. For example, W can be an o-, m- or p-phenylene radical. Other suitable radicals are cycloalkyldiyl radicals, in particular cyclopentyldiyl and cyclohexyldiyl. Suitable aryidiyl groups are, for example, 1,1'-biphenylene radicals, naphthylene radicals, oxydiphenylene radicals, diphenylmethanediyl radicals, diphenylethanediyl radicals, diphenylpropanediyl radicals and ferrocenediyl radicals. Examples of suitable phosphabenzene compounds are given in DE-A 196 21 967 mentioned above:

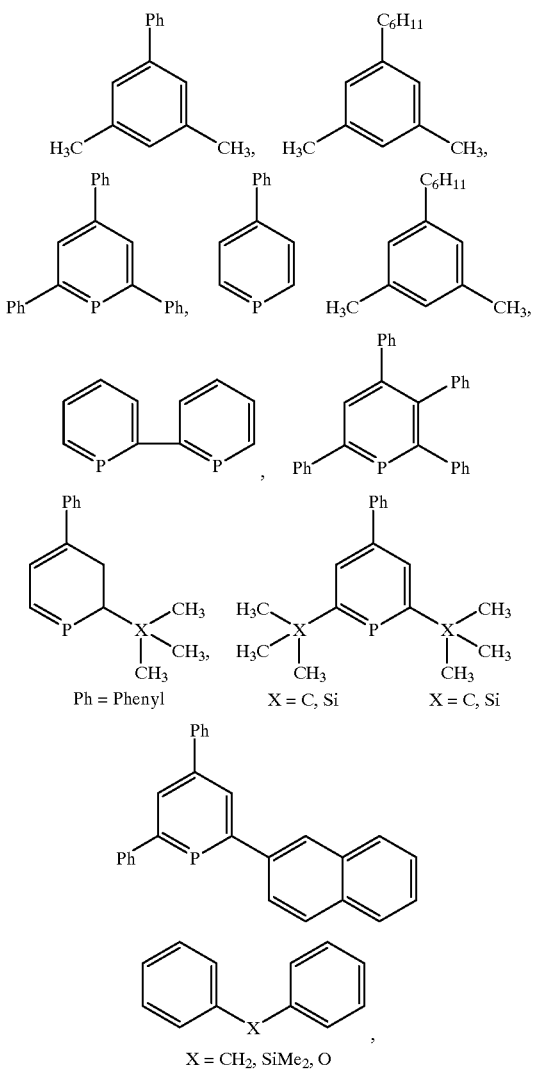

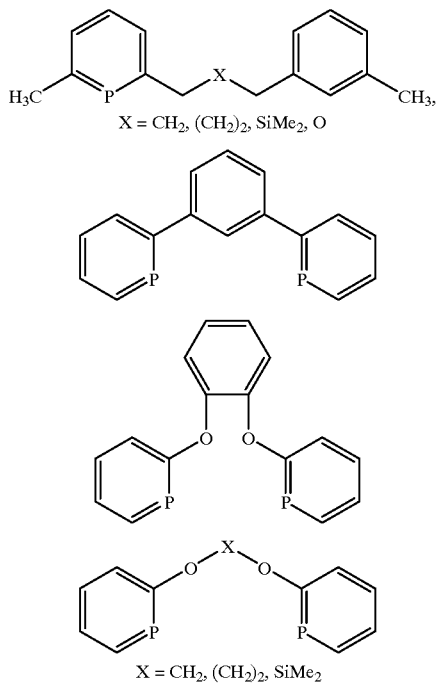

The pyrilium salts employed in the direct reaction with $PH_3$ can be obtained, for example, as described in Houben-Weyl, Hetarenes II, Part 2, editor R. Kreher, Volume E7b, pages 755 ff., Thieme Verlag, Stuttgart.

The invention also relates to some of the phosphabenzene compounds described above:

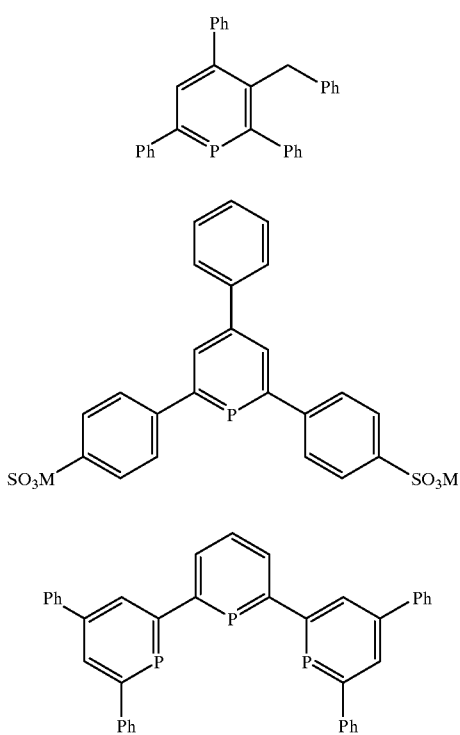

in which Ph is a phenyl radical and M is hydrogen or an alkali metal.

The compounds prepared in accordance with the invention can be used for the preparation of complexes withi metals from sugroup VIII of the Periodic Table of the Elements. These complexes can be employed as cocatalysts in hydroformylation reactions. Suitable reaction conditions are described in DE-A 196 21 967:

The active catalysts are those of the formula $M(L)_n(CO)_m$, where M is at least one central atom of an element from sub-group VIII of the Periodic Table of the Elements, L is at least one ligand of the formulae I to IV, n and m are each at least 1, and where n and m are each, for example, the numbers 1 and 3 per equivalent of M and the sum n+m is from 2 to 5, and where further radicals, such as hydrido, alkyl or acyl, may be present as ligands.

The active carbonyl complex is generally prepared in situ, i.e. in the hydroformylation reactor, from a salt or compound of the metal M, the ligand and carbon monoxide; however, it can also be prepared separately and employed as such.

The complex catalysts preferably consist of a central atom, M, selected from the transition metals cobalt, ruthenium, rhodium, palladiun and platinum, but in particular cobalt and rhodium, complexed with carbonyl and hydrido, alkyl or acyl radicals and, as ligands, the preferred monodentate or polydentate phosphabenzenes used in accordance with the invention If the complex catalysts are generated in situ, simple precursor complexes, such as biscarbonylrhodiurn acetylacetonate or rhodium acetate, are subjected to the reaction conditions in the presence of the corresponding ligands, or activating additives, for example Bronsted or Lewis acids or bases, are added to the precursor complexes.

For in-situ formation of the catalyst in the reaction mixture, the ligand is employed in a molar ratio (calculated as equivalents of phosphorus) to rhodium of from 1:1 to 1000:1, and in addition an inert solvent is used. Particularly preferred solvents are the aldehydes formed by reaction of the respective olefin, and the high-boilers inherent in the synthesis, which are formed by subsequent reactions of the respective aldehyde in the hydroformylation process. In the case of ligands which have been hydrophilized by suitable substituents, preference is given to water, alcohols or other polar solvents.

The composition of the synthesis gas $CO/H_2$ employed in the novel hydroformylation process can be varied within a broad range. For example, synthesis gas having a $CO/H_2$ molar ratio of from 5:95 to 70:30 can be employed successfully. Preference is given to synthesis gas having a $CO/H_2$ ratio of from 40:60 to 60:40. Particular preference is given to a $CO/H_2$ ratio of about 1:1.

The hydroformylation reaction with the catalyst is preferably carried out at between 20 and 180° C., in particular at from 50 to 150° C. However, an optimum temperature is determined experimentally for each catalyst system. The reaction pressure can vary, depending on the cocatalyst, i.e. ligand, and substrate, in the range from atmospheric pressure up to 700 bar, preferably up to 300 bar, the term low-pressure reactions normally denoting reactions carried out at a pressure in the range up to about 30 bar, the term medium-pressure reactions normally denoting reactions carried out at a pressure in the range up to about 100 bar and the term high-pressure reactions normally denoting reactions carried out at a pressure above 100 bar.

The reaction is generally carried out with the catalyst dissolved homogeneously in the reaction medium; the catalyst is separated off from the hydroformylation reaction product and fed back into the hydroformylation step.

In general, the corresponding aldehydes are obtained virtually exclusively, in excellent yields.

Olefins which can be hydroformylated in accordance with the invention are á-olefins or internal olefins or internal, branched olefins. For example, specific mention may be made of the following olefins: ethylene, propene, 1-butene, 1-octene, $C_{5-20}$-á-olefins, linear, internal $C_{5-20}$-olefins, 2-butene; branched, internal octene mixtures; branched, internal nonene mixtures; branched, internal dodecene mixtures, cyclohexene, á-pinene, styrene, 4-isobutylstyrene, methyl 3-pentenoate, methyl 4-pentenoate, methyl oleate, 3-pentenenitrile, 4-pentenenitrile, 2,7-octadien-1-ol, 7-octenal, methyl acrylate, methyl methacrylate, acrylonitrile, vinyl acetate, vinyl glycol diacetate, vinyl methyl ether, polypropene and polyisobutylene. Other suitable substrates are dienes and polyenes containing isolated or conjugated double bonds. Examples are 1,3-butadiene, 1,5-hexadiene, vinylcyclohexene, dicyclopentadiene, 1,5,9-cyclooctatriene, butadiene homopolymers and copolymers, and polyisobutene.

In addition, the hydroformylation reaction is carried out in a manner known per se. Details on the reaction procedure are given in Beller, et al., Journal of Molecular Catalysis A: 104 (1995) 17–85, and Falbe, Ed. New Syntheses with Carbon Monoxide, Springer, Berlin, 1980, pp. 5 ff.

The invention is illustrated in greater detail below with reference to examples:

EXAMPLES 1 to 6

2,4,6-Triphenylphosphabenzene 2,4,6-Triphenylphosphabenzene was prepared from commercially available 2,4,6-triphenylpyrilium tetrafluoroborate salt (Aldrich) with the aid of $PH_3$. The salt was employed in an amount of 4 mmol or 63 mmol respectively. All experiments were carried out in an autoclave (material HC) with a capacity of 300 ml. The autoclave was charged with 100 g or 150 g respectively of n-butanol as solvent and 0.5 g or 1.0 g respectively of hydrogen bromide in acetic acid (30% by weight, Aldrich) as catalyst and flushed with 5 bar of nitrogen. The gas space was then flushed once with $PH_3$. 5 bar of $PH_3$ were then injected at room temperature, and injection of $PH_3$ was continued until the pressure remained constant at 5 bar. The reaction mixture was then heated to a reaction temperature of 110° C., and the solution was stirred vigorously with a gas-diffsion stirrer. An autogenous pressure of 12 bar became established. The reaction was then carried out at a pressure of 12 bar, the pressure in the reactor being held at the desired pressure level during the reaction by re-injection via a pressure regulator. Other reactions were carried out at a different pressure by injecting $PH_3$. After the reaction time, the autoclave was cooled, decompressed, flushed thoroughly with nitrogen while stirring, and dismantled. The autoclave products were evaporated to half and crystallized out overnight in the refrigerator. The crystals were filtered off with suction, washed three times with pentane and dried. The crystals and the mother liquors were weighed, and the phosphabenzene proportion was determined by gas chromatography using an internal standard and correction factors. The results are shown in the table below.

| Ex. | Amount g(mmol) | Time h | Pressure bar | Ligand content in the solid % by weight | Weight of solid g | Yield of solid % | Yield of solid + mother liquor % |
|---|---|---|---|---|---|---|---|
| 1 | 1.58 (4) | 1 | 10.8 | 99.8 | 0.78 | 60 | 68 |
| 2 | 1.58 (4) | 4 | 10.4 | 100.0 | 0.91 | 70 | 78 |
| 3 | 1.58 (4) | 41 | 10.5 | 99.9 | 0.92 | 71 | 78 |
| 4 | 1.58 (4) | 1 | 20 | 99.9 | 1.00 | 77 | 86 |
| 5 | 1.58 (4) | 1 | 30 | 99.9 | 1.00 | 77 | 82 |
| 6 | 25 (63) | 4 | 30 | 99.9 | 16.6 | 77 | 79 |

The results show that the reaction can be carried out quickly and economically. At shorter reaction times, a higher $PH_3$ pressure is preferred.

EXAMPLE 7

Pyrilium Salt for the Preparation of 2,4,6-triphenyl-3-benzylphosphabenzene

The synthesis of the 2,4,6-triphenyl-3-benzylpyrilium tetrfiuoroborate salt from 1,3-diphenyl-3oxopropene (chalcone) was carried out as described in Houben-Weyl, Volune E7b, page 855, for the 2,4,6-triphenylpyrilium tetafluoroborate salt, without addition of acetophenone.

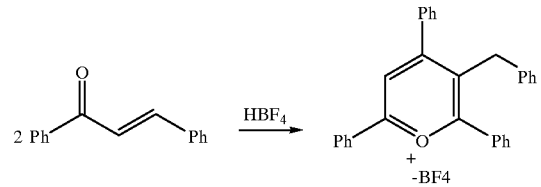

EXAMPLE 8

Pyrilium Salt for the Preparation of 1,3-bis(4,6-diphenyl-2-phosphaphenyl)benzene The synthesis of the 1,3-bis(4,6-diphenyl-2-pyrilium) benzene bistetrfuoroborate was carried out as follows:

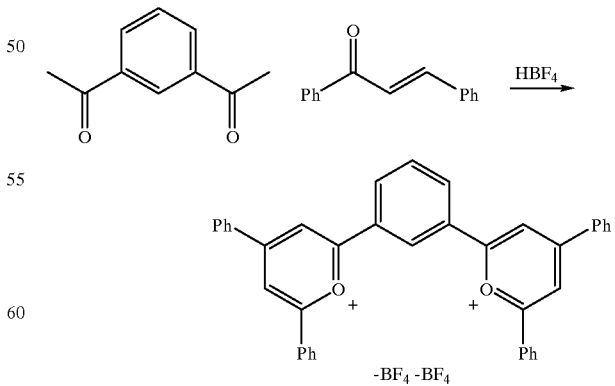

1,3-Diacetylbenzene (1.00 g, 6.17 mmol) and chalcone (5.10 g, 24.7 mmol) were dissolved in 10 ml of 1,2-dichloroethane, and the mixture was warmed to 70° C.

Tetrafluoroboric acid diethyl etherate (4.02 g, 24.7 mmol) was added, and the solution was refluxed for 2 hours. The reaction mixture was cooled to room temperature and filtered, and 20 ml of diethyl ether were added to the filtrate. The precipitated solid was taken up in a little methylene chloride and precipitated using ethanol. The combined solids were recrystallized from ethanol. Yield: 35 to 40%.

EXAMPLE 9

Pyrilium Salt for the Preparation of 2,6-(4-sulfonatophenyl)-4-phenylphosphabenzene The synthesis of 2,6-(4-sulfonatophenyl)-4-pyrilium tetrafluoroborate salt was carried out in two steps as follows:

Step 1: Synthesis of 3-(4-sulfonatophenyl)-3-oxo-1-phenylpropene

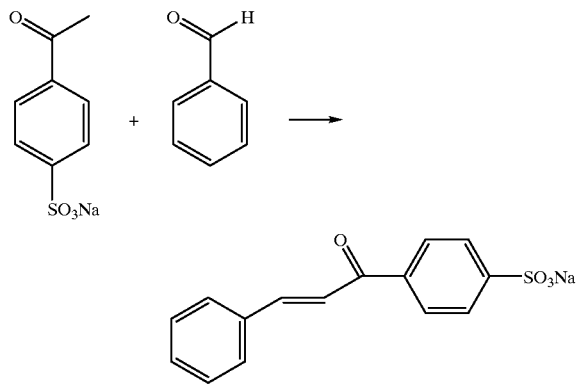

Sodium 4-acetoxybenzenesulfonate (22.2 g, 0.1 mol) was dissolved in 100 ml of water, and the mixture was heated to 50° C. A solution of 0.2 g of NaOH in 100 ml of methanol and benzaldehyde (10.6 g, 0.1 mol) was added. A solid precipitated and, after being stirred for 3 hours at room temperature, was filtered off with suction. The solid was washed 3 times with diethyl ether. Yield: 77%.

Step 2: Synthesis of 2,6-(-4-sulfonatophenyl)-4-phenylpyrilium tetrafluoroborate

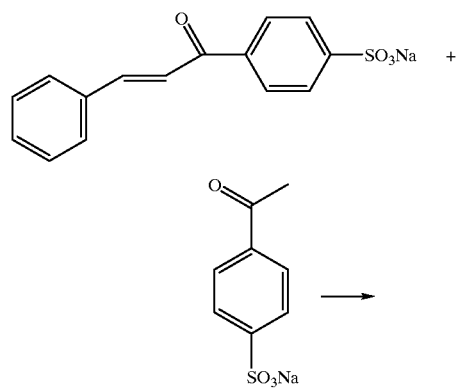

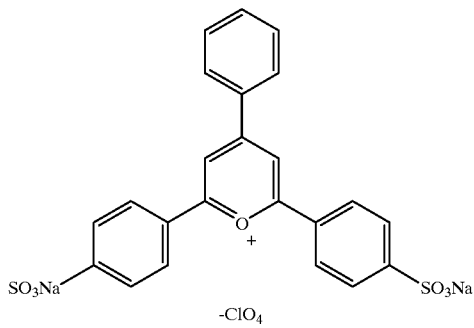

3-(4-Sulfonatophenyl)-3-oxo-1-phenylpropene (3.1 g, 0.01 mol) and sodium acetoxybenzenesulfonate (2.22 g, 0.01 mol) were mixed, and 2 ml of water were added to the mixture. Perchloric acid (10 ml) was then added dropwise. An intensely yellow suspension formed. The suspension was heated to 90° C. and stirred for 2 hours, during which a homogeneous solution formed. After the mixture had been cooled to room temperature, some of the product precipitated as a solid and was separated off by filtration, washed 3 times with cooled I-butanol and dried at 80° C. and 6 mbar. The supernatant solution was added dropwise to cooled 1-butanol, whereupon furler product precipitated and was filtered off and worked up like the first fraction. Yield: 3.1 g of yellow-green, water-soluble solid.

EXAMPLES 10 to 14

$PH_3$ reactions

All experiments (batchwise) were carried out in a 300 ml autoclave (material HC). The autoclave was charged (solvent: n-butanol, 100 g; catalyst: hydrobromic acid in acetic acid (30% by weight, Aldrich), 0.5 g) and flushed with 5 bar of $N_2$. The gas space was then flushed once with $PH_3$. 5 bar of $PH_3$ were injected at room temperature, and $PH_3$ was re-injected until the pressure remained constant at 5 bar. The reaction mixture was heated to the reaction temperature, and the solution was stired vigorously using a gas-dispersion stirrer. An autogenous pressure of 10.5 bar became established. The reaction was then carried out at this pressure or if desired at a higher pressure by injecting $PH_3$. The pressure in the reactor was held at the desired pressure level during the reaction by re-injection via a pressure regulator. After the reaction time, the autoclave was cooled, decompressed, flushed thoroughly with $N_2$ with stirring and dismantled.

| Ex. | Pyrilium salt | Amount g | Time h | Temp. °C. | Pressure bar | Phosphabenzene yield |
|---|---|---|---|---|---|---|
| 10 | 2,4,6-Triphenylpyrilium hydrogensulfate (Aldrich) | 1.6 | 1 | 110 | 10.5 | 63 |
| 11 | 2,4,6-Triphenyl-3-benzylpyrilium tetrafluoroborate | 1.9 | 1 | 110 | 10.5 | 63 |
| 12 | 2,4,6-Triphenyl-3-benzylpyrilium tetrafluoroborate | 1.5 | 4 | 120 | 30 | 72 |
| 13 | 1,3-Bis(4,6-diphenylpyrilium) benzene bistetrafluoroborate | 2.5 | 4 | 120 | 30 | 65 |
| 14 | 2,6-(4-Sulfonatophenyl)4-phenyl-pyrilium tetrafluoroborate | 1.3 | 4 | 110 | 10.5 | aqueous solution $^{31}$P-NMR 185 ppm |

What is claimed is:

1. A process for the preparation of phosphabenzene compounds of the formulae I and II

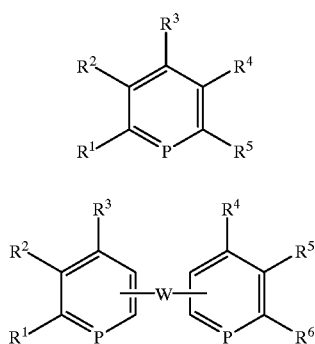

where $R^1$ to $R^6$, independently of one another, are hydrogen, COOM, SO$_3$M, NR$_3$X, NR$_2$, OR, COOR, SR, C$_1$–C$_{12}$-alkyl, C$_6$–C$_{12}$-aryl, C$_7$–C$_{12}$-aralkyl, or C$_{3-6}$-heterogcycoalkyl having 1 to 3 heteroatoms, and wherein C$_1$–C$_{12}$ -alkyl, C$_6$–C$_{12}$-aryl, C$_7$–C$_{12}$-aralkyl, or C$_{3-6}$-heterocycloalkyl are optionally substituted by COOM, SO3M, NR$_3$X, NR$_2$, OR, COOR or SR M is hydrogen, NH$_4$ or an alkali metal, X is an anion, R is hydrogen, C$_{1-6}$-alkyl, or C$_{1-12}$-alkyl, C$_{6-12}$-aryl, C$_{7-12}$-aralkyl or C$_{3-6}$-heterocycloalkyl having 1 to 3 heteroatoms optionally substituted by the above radicals $R^1$ to $R^6$ or linked to form fused rings, and —W— is a bridge selected from a covalent bond, an oxo group, a sulfur group, an amino group, a di-C$_{1-6}$-alkylsilicon group or a C$_{1-16}$-radical optionally part of one or more linked cyclic or aromatic rings and optionally interrupted by 1 to 3 heteroatoms, where the phosphabenzene ring o- or m-position not bonded to the bridge may carry one of the radicals $R^1$ to $R^6$, with the exception of bis-3,3'-(2,4,6-triphenyl-3-phosphabenzene)-1,1 -biphenyl, by reacting corresponding pyrylium salts with PH$_3$ in the presence of a catalytic amount of acid and in the presence or absence of a solvent or diluent wherein the pyrilium salts are mixed with PH$_3$ at above 0° C. and reacted at from 0° C. to 200° C. and at a pressure greater than 1 bar wherein PH$_3$ is passed into the reaction mixture during the reaction in order to keep the PH$_3$ partial pressure essentially constant.

2. A process as claimed in claim 1, wherein the reaction is carried out at a PH$_3$ partial pressure in the range from 0.1 to 100 bar.

3. A process as claimed in claim 1, wherein the reaction is carried out at a pressure of from 5 to 35 bar.

4. A process as claimed in claim 1, wherein the pyrylium salts are mixed with PH$_3$ at ambient temperature, and the resultant mixture is heated to a temperature in the range from 110 to 130° C. for the reaction.

5. A process as claimed in claim 1, wherein the radicals $R^1$ to $R^6$ in the compounds of the formulae I and II are phenyl radicals or benzyl radicals, optimally substituted by SO$_3$M.

6. A process as claimed in claim 1, wherein the pyrylium salts are tetrafluoroborates, perchlorates, hydrogensulfates, bronides, iodides or mixtures thereof.

7. A process as claimed in claim 1, wherein, after the reaction, the reaction mixture is decompressed and, flushed with an inert gas, the gases leaving the reaction mixture being cooled and passed through a separator in order to removed unreacted PH$_3$ in liquid form, and the PH$_3$ removed is fed back into the reaction.

8. A compound of the formula III, IV or V

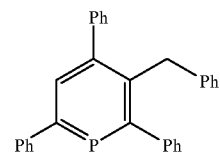

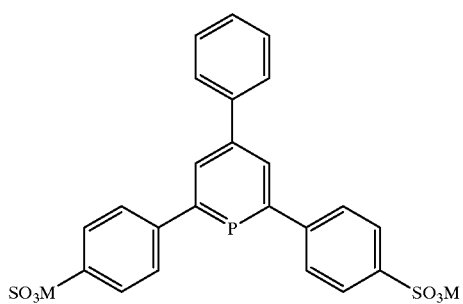

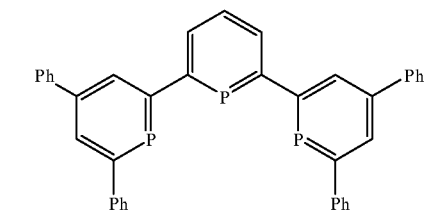

where Ph is a phenyl radical, and M is hydrogen or an alkai metal.

* * * * *

UNITED STATES PATENT AND TRADEMARK OFFICE
CERTIFICATE OF CORRECTION

PATENT NO. : 6,255,532 B1
DATED : July 3, 2001
INVENTOR(S) : Paciello et al.

It is certified that error appears in the above-identified patent and that said Letters Patent is hereby corrected as shown below:

Column 11, claim 1,
Line 38, "$C_{3-6}$-heterogcycoalkyl" should be -- $C_{3-6}$-heterocycloalkyl --.
Line 41, "SO3M" should be -- $SO_3M$ --.

Column 12, claim 6,
Line 26, "bronides" should be -- bromides --.

Signed and Sealed this

Twenty-second Day of January, 2002

Attest:

Attesting Officer

JAMES E. ROGAN
*Director of the United States Patent and Trademark Office*